(12) United States Patent
Boulton et al.

(10) Patent No.: US 6,500,390 B1
(45) Date of Patent: Dec. 31, 2002

(54) METHOD FOR SEALING AND VENTING A MICROPLATE ASSEMBLY

(76) Inventors: David A. Boulton, 146 Hope Rd., Tinton Falls, NJ (US) 07724; Carolyn I. Solewski, 146 Hope Rd., Tinton Falls, NJ (US) 07724

( * ) Notice: Subject to any disclaimer, the term of this patent is extended or adjusted under 35 U.S.C. 154(b) by 0 days.

This patent is subject to a terminal disclaimer.

(21) Appl. No.: 09/460,135

(22) Filed: Dec. 13, 1999

Related U.S. Application Data

(63) Continuation-in-part of application No. 08/953,441, filed on Oct. 17, 1997, now Pat. No. 6,027,694.
(60) Provisional application No. 60/028,587, filed on Oct. 17, 1996.

(51) Int. Cl.[7] .............................. B01L 3/02; B01L 3/14; B65D 41/60
(52) U.S. Cl. ...................... 422/100; 422/102; 277/312; 277/315; 215/247; 215/249; 220/524; 220/525; 220/526
(58) Field of Search ................... 29/448; 220/203.08, 220/513, 526, 523–525, 203.16–203.17; 422/99, 104, 102, 100; 215/247, 248, 261, 249, 250–251, 256, 253; 277/309, 311, 315, 312, 314, 307, 308, 364, DIG. 3, 355

(56) References Cited

U.S. PATENT DOCUMENTS

| | | | | |
|---|---|---|---|---|
| 4,134,512 A | * | 1/1979 | Nugent | |
| 4,349,035 A | * | 9/1982 | Thomas et al. | |
| 4,515,752 A | * | 5/1985 | Miramanda | 422/99 |
| 4,885,253 A | * | 12/1989 | Kralovic | |
| 5,202,093 A | * | 4/1993 | Cloyd | 422/102 |
| 5,264,184 A | * | 11/1993 | Aysta et al. | 422/101 |
| 6,027,694 A | * | 2/2000 | Boutlon et al. | 422/102 |
| 6,361,744 B1 | * | 3/2002 | Levy | 422/99 |

* cited by examiner

*Primary Examiner*—Matthew O. Savage
*Assistant Examiner*—Marianne Ocampo
(74) *Attorney, Agent, or Firm*—Michaelson & Wallace; Peter L. Michaelson; Jeremiah G. Murray

(57) ABSTRACT

A microplate assembly comprising a multi-well microplate, a plurality of vent caps and a porous vent film. The microplate includes a frame that houses a plurality of open wells in a rectangular array. Vent caps mount on the microplate to seal and vent the wells. When the vent caps are coupled to the wells, an interior volume is formed in each well. The wells function as a vessel for liquid samples that occupy predetermined spaces within the interior volumes. Each liquid sample remains within its predetermined space for all orientations of the microplate assembly. The vent cap comprises an array of well inserts. Each well insert comprises a sealing plug and a vent tube. A flexible perforated web interconnects the well inserts to each other. The vent tubes are fixed to the sealing plugs and terminate in a vent. A barrier formed from a plurality of nested flaps resiliently mounts on the vent tube to partially cover the vent and help inhibit the evaporation and loss of the liquid samples.

5 Claims, 11 Drawing Sheets

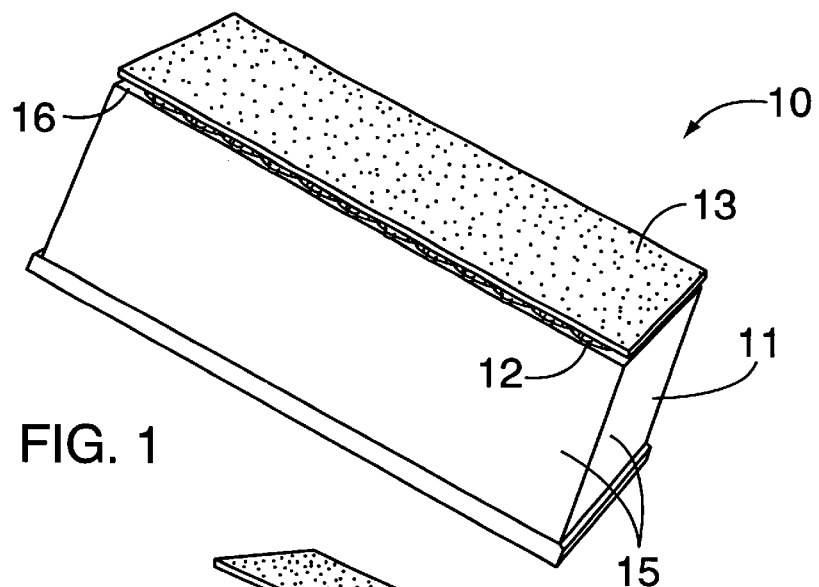
FIG. 1
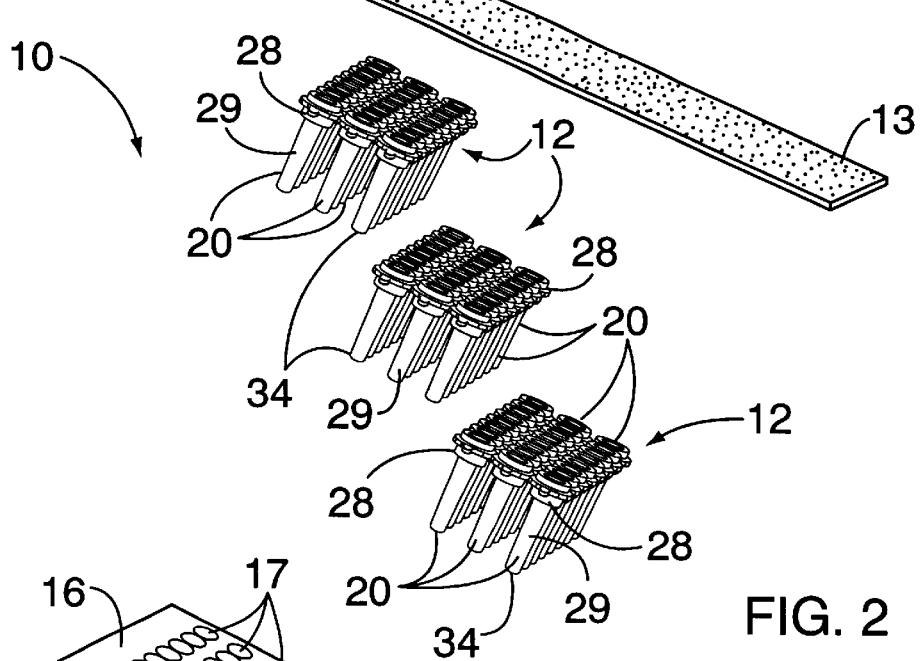
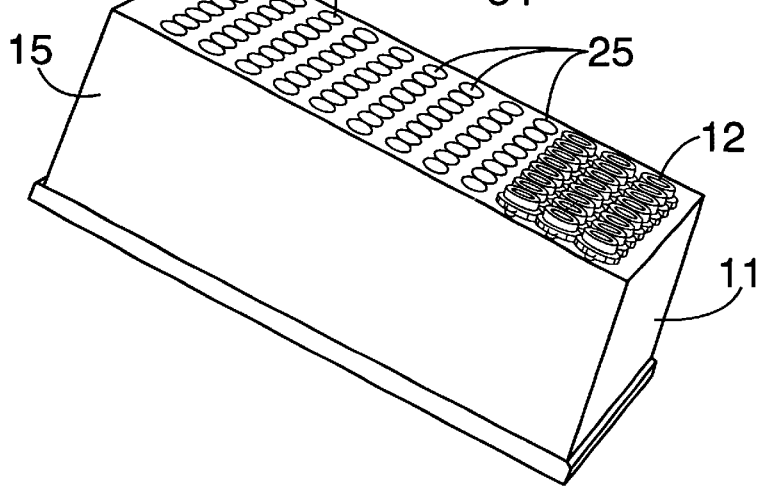
FIG. 2

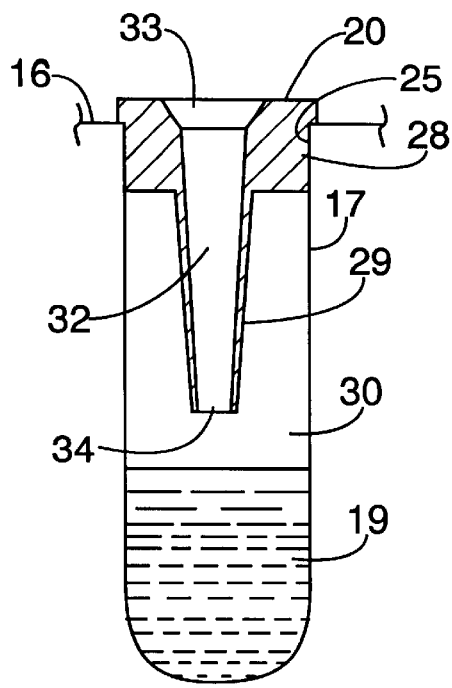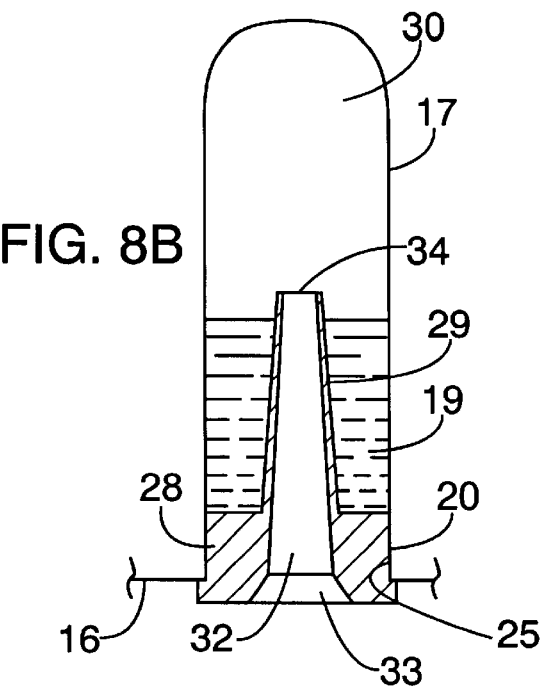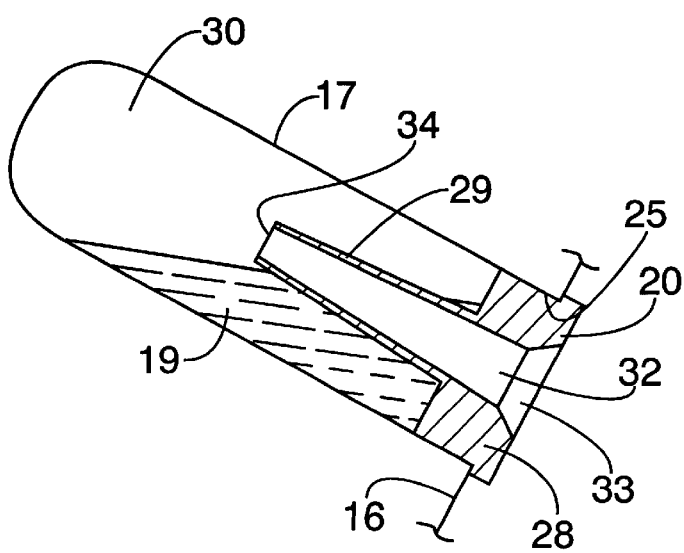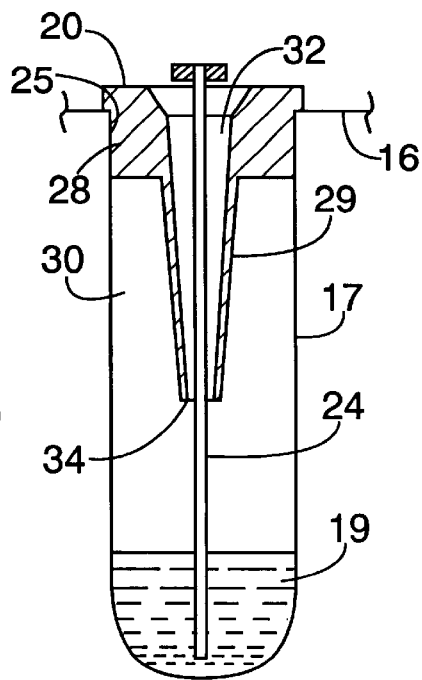

METHOD FOR SEALING AND VENTING A MICROPLATE ASSEMBLY

CROSS-REFERENCE TO RELATED APPLICATIONS

This is a continuation-in-part application of our U.S. patent application Ser. No. 08/953,441, filed on Oct. 17, 1997 now U.S. Pat. No. 6,027,694 issued on Feb. 22, 2000 which claims the benefit of provisional application 60/028,587 filed Oct. 17, 1996.

BACKGROUND OF THE INVENTION

1. Field of the Invention

The present invention relates generally to techniques for handling fluid samples in chemical, biological, pharmacological and related processes. More particularly, it relates to spillproof microplate apparatus for receiving and securely holding fluid samples.

2. Description of the Prior Art

Multi-well microplates play an important role in conventional chemical, biological, pharmacological and related processes that are designed to analyze and/or synthesize large numbers of small fluid samples. Such conventional processes normally employ multi-well microplates as tools when processing, shipping and storing the small liquid samples. Many of these processes achieve high-throughputs by applying modern automation techniques, including robotics. In recent years, efforts have been directed at integrating the different prevailing microplate apparatus into the automation equipment of these high-throughput processes. Such integration efforts, however, have had only limited success. Specifically, spillage, leakage, evaporation loss, airborne contamination and inter-well cross contamination of liquid samples are some of the common deficiencies that limit the application of many standard microplate assemblies in high-throughput systems. Consequently, one of the most critical problems confronting designers of microplate apparatus has been finding techniques of preventing the loss and contamination of well contents without unduly complicating the structures and/or handling requirements of a microplate assembly.

A standard microplate assembly normally comprises a microplate having a plurality of open wells and a closure device for sealing the wells shut. Commonly available microplates generally embody a unitary molded structure comprising a rigid frame for housing a plurality of open wells arranged in a rectangular array. Standard well closures include resilient, press-fit stoppers, rigid screw caps, adhesive films and the like. Microplates come in a range of sizes; a well may be sized to hold as high as five milliliters or as low as only a few microliters of liquid. In addition, microplates come in a variety of materials, such as polystyrene, polycarbonate, polypropylene, Teflon, glass, ceramics and quartz. Conventional microplates found in many high-throughput systems comprise a 96-well geometry molded into an 8×12 rectangular array of open wells. Microplates with lower well densities (e.g., 24 and 48 wells) and higher well densities (e.g., 384 and 864 wells) are also available.

An important microplate application exists in high-throughput organic synthesis (HTOS) systems. HTOS has been rapidly gaining importance as a tool for the accelerated synthesis of small organic molecules. HTOS systems employ a variety of automation techniques, which significantly reduce the time required for the development of commercially acceptable compounds in the pharmaceutical, agrochemical and other specialty chemical industries. Most conventional HTOS systems simultaneously synthesize large groups of compounds while using standard microplate assemblies for the reaction, purification and shipment of such compounds. Another important microplate application exists in high-throughput screening (HTS) systems, which examine samples of pre-dissolved compounds for desired properties. HTS systems usually examine the samples while they are contained in the wells of conventional microplates. As such, automatic apparatus must manipulate conventional microplates and their contents during a typical HTS process. Consequently, a primarily requirement of a microplate assembly for use in HTOS and HTS systems is an ability to securely maintain a controlled environment for a liquid sample while the assembly is being manipulated in an automation process. In addition, a microplate assembly must provide means for adding reagents or other materials to an individual well or to multiple wells simultaneously. Further, a microplate assembly must allow for the mechanical mixing of well contents without risking spills, leaks or cross contamination.

Many HTOS systems deliver multiple samples as solutions of pre-dissolved compounds in microplate assemblies to various locations throughout the world. To prevent a loss of these solutions of pre-dissolved compounds from occurring during delivery, suppliers often convert the solutions into solids prior to shipment by freezing or other methods. Shipping compounds as solids rather than liquids, however, creates problems in dissolution that can complicate and inhibit subsequent sample evaluation procedures. Further, an unstable solid material may disperse on opening of a closed well prior to re-dissolution. Consequently, those skilled in the art have recognized that HTOS systems should preferably deliver solutions of compounds in their stable liquid form.

A need to deliver compounds as stable liquids creates handling and storage requirements that standard microplate apparatus cannot fully provide. As mentioned above, spills, leaks, sample evaporations and well contamination often limit the application of most standard microplate assemblies in high-throughput systems. A singular example involves the shipping of microplate assemblies in aircraft cargo hulls. At flying altitudes, a low ambient air pressure in an aircraft cargo hull may create a relatively large pressure difference across a well closure. Such pressure differences often cause press-fit closures to distort or even pop open, thereby permitting a resident liquid sample to spill, leak, evaporate, and/or cross contaminate other open wells. Similar problems also occur in conventional surface shipping because of mechanical shocks, vibrations and the like. Likewise, some chemical reactions create heat and pressure of sufficient magnitude in the confines of a sealed well such that the well closure will inadvertently open, thereby causing a resident sample to leak.

One attempt to resolve the shipping problems described above involves the use of a solution of a compound in an assay-compatible solvent that can be frozen, such as dimethyl sulfoxide. If the solution remains frozen, delivery may be achieved without spillage. This, unfortunately, is not always the case, since the useful life of cooling agents available for use in shipping environments rarely exceeds a few days. In addition, certain compounds will come out of solution on freezing and remain out on thawing, further complicating the use of cooling agents. Therefore, shipping techniques that involve cooling agents often create multiple sample-handling problems and require an inspection step prior to assay. Other attempts at solving these and similar problems have usually resulted in unduly complicating the structure of a microplate assembly while imposing elaborate and unacceptable requirements on automated processing systems.

SUMMARY OF THE INVENTION

The present invention solves these problems in the art by providing a technique for preventing the loss and contamination of the contents of microplate assemblies. In general, the present invention includes a method of sealing and venting a vessel having an opening and an interior volume containing a liquid sample. The method comprises the steps of inserting a plug in the opening, forming a vent in the interior of the vessel, and extending a tubular passage from the vent to the exterior of the vessel. The vent communicates with the interior volume and the exterior of the vessel. The method further includes extending the tubular passage through the plug. In addition, the liquid sample is deposited in a liquid-holding space in the interior volume. The liquid sample remains confined to the liquid-holding space for all orientations of the vessel. The vent communicates with the interior volume outside the liquid-holding space. A resilient barrier, having a plurality of nested flaps separated via narrow slits, mounts at one end of the tubular passage to inhibit the loss of a liquid sample via evaporation, spillage and the like while permitting the insertion of a probe into the interior volume.

According to another aspect of the invention, a microplate assembly comprises a microplate having a plurality of open wells. Each of the wells comprises a vessel with an interior volume. A seal is coupled to the wells for sealing the wells so that liquid in the interior volume is prevented from exiting the wells. A vent equalizes the pressure of the wells with the ambient pressure. The vent includes a resilient barrier with a plurality of nested flaps separated via narrow slits. The flaps resiliently mount at one end of the tubular passage to inhibit the loss of liquid sample via evaporation, spillage and the like while permitting the insertion of a probe into the interior volume.

Still, another aspect of the invention includes a microplate assembly comprising a multi-well microplate, a plurality of vent caps and a porous vent film. The microplate houses a plurality of open wells in a rectangular array. Vent caps seal and vent the wells. When the vent caps are coupled to the wells, an interior volume is formed in each well. The wells hold liquid samples that occupy predetermined spaces within the interior volumes. The liquid samples remain within a predetermined space for all orientations of the microplate assembly. The vent caps comprise sealing plugs and vent tubes, which are interconnected by a perforated web. The sealing plugs form a seal at the mouth of the open wells. The vent tubes attach to the sealing plugs and terminate in vents defined by a plurality of flaps separated by narrow slits. The vents communicate with the interior volumes outside the predetermined spaces occupied by the liquid samples. The vents permit the pressure within the interior volume to be equalized with the ambient pressure via a passage that runs through the vent tube and the sealing plugs. Material may be added to or removed from the wells via the passages and the resilient flaps. The porous vent film, which has an adhesive coating, adheres to the vent caps while covering the passages, thereby inhibiting evaporation of the liquid samples.

BRIEF DESCRIPTION OF THE DRAWINGS

The teachings of the present invention can be readily understood by considering the following detailed description in conjunction with the accompanying drawings, in which:

FIG. 1 is a pictorial view of a microplate assembly in accordance with the present invention;

FIG. 2 is an exploded pictorial view of the microplate assembly of FIG. 1, showing a vent film, four vent caps and a microplate in accordance with the present invention;

FIG. 8A depicts a diagrammatic cross-section of a well, illustrating the position of a liquid sample when the well assumes an upright position;

FIG. 8B depicts a diagrammatic cross-section of a well, illustrating the position of a liquid sample when the well assumes an inverted position;

FIG. 8C depicts a diagrammatic cross-section of the well in FIGS. 8A and 8B, illustrating the position of a liquid sample when the well assumes an inclined position;

FIG. 9 depicts a diagrammatic cross-section of a probe inserted in a well;

DETAILED DESCRIPTION OF THE PREFERRED EMBODIMENT

Figure 3:
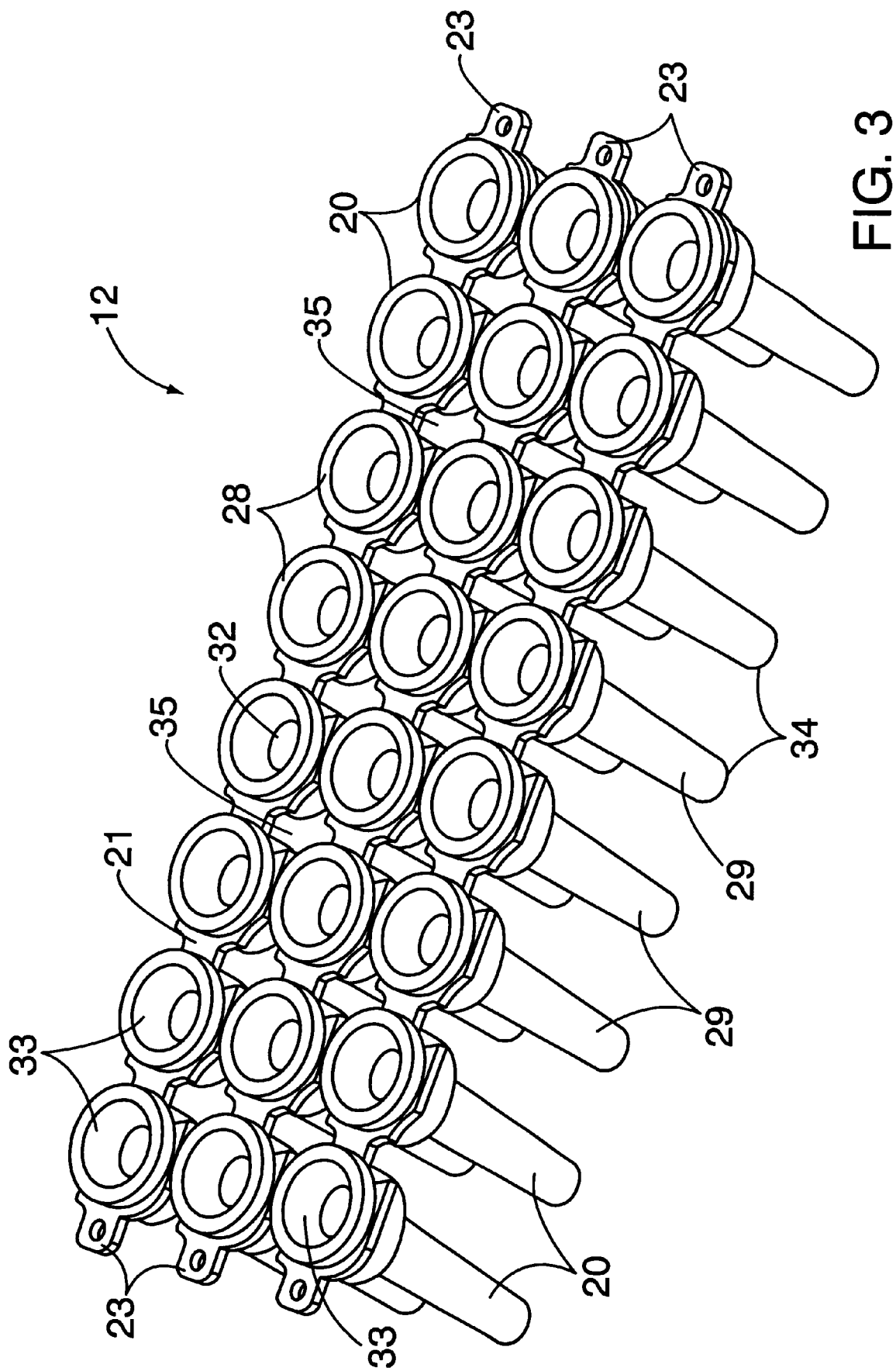
FIG. 3 is a pictorial view of a vent cap viewed from above, which forms a part of the microplate assembly illustrated in FIGS. 1 and 2.
Figure 4:
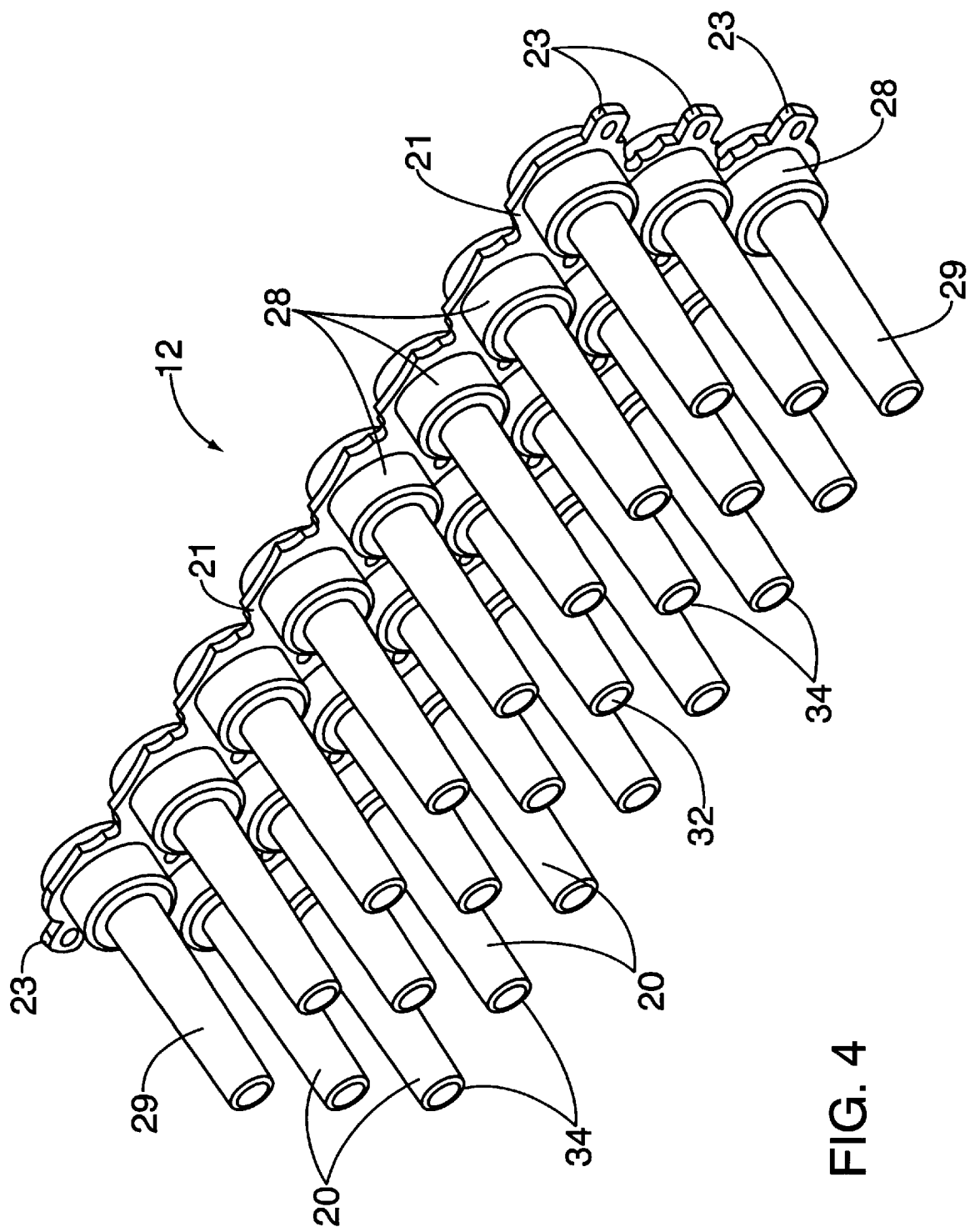
FIG. 4 illustrates the vent cap of FIG. 3 in a pictorial view as seen from below.
Figure 5:
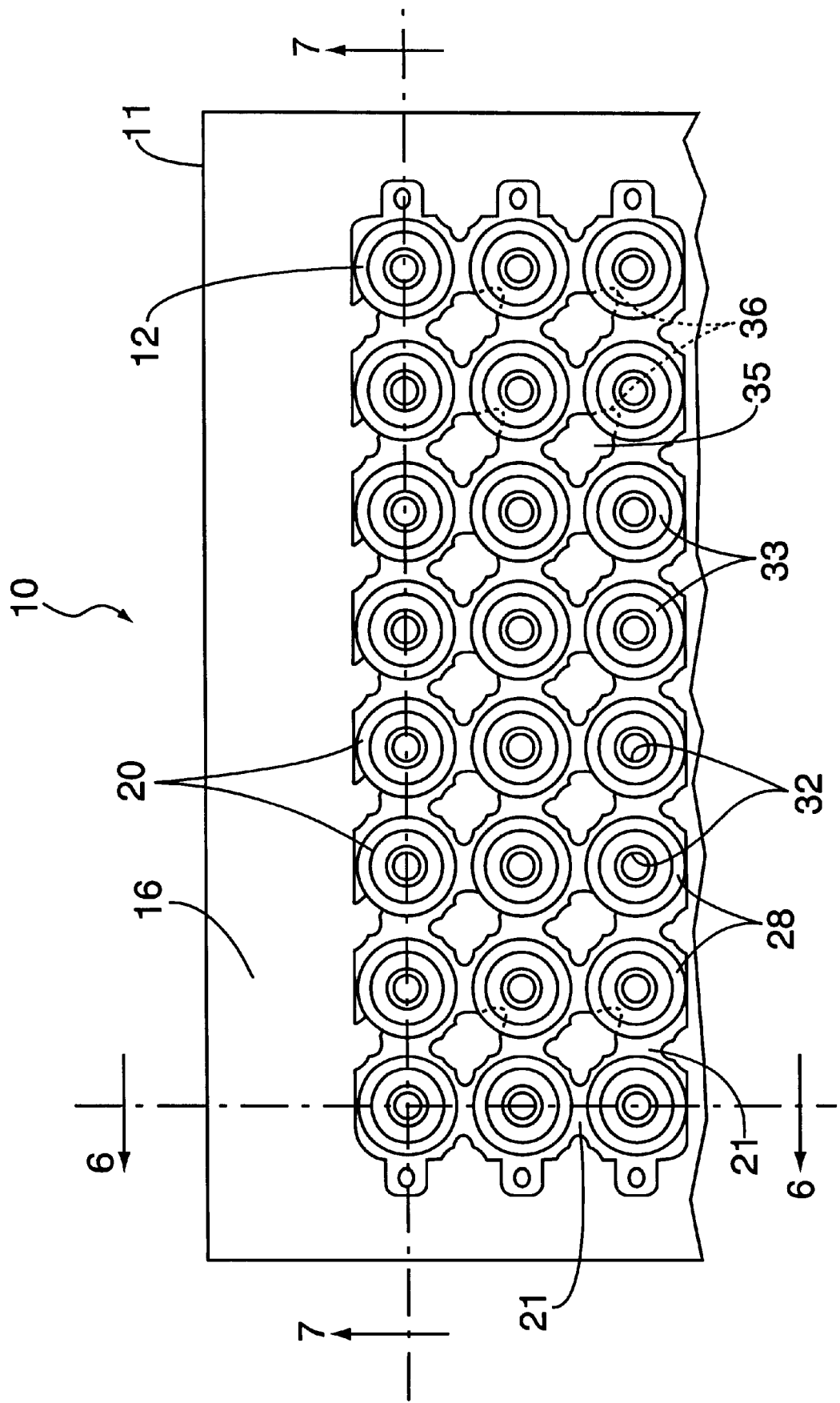
FIG. 5 depicts a break-away, top plan view of a portion of the microplate assembly of FIGS. 1 and 2.
Figure 6:
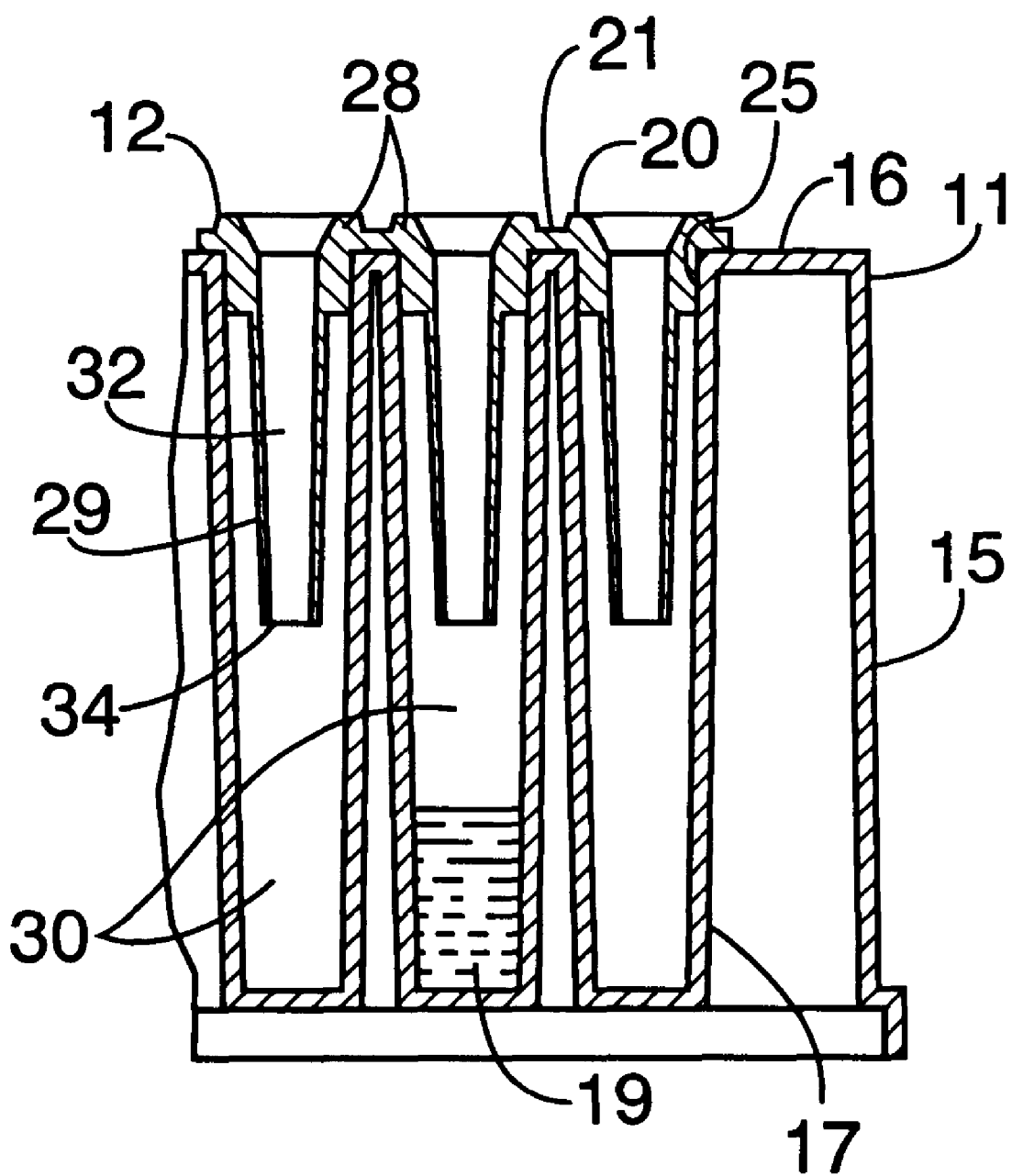
FIG. 6 is an elevation in cross section taken on the line 6—6 of FIG. 5 and looking in the direction of the arrows.
Figure 7:
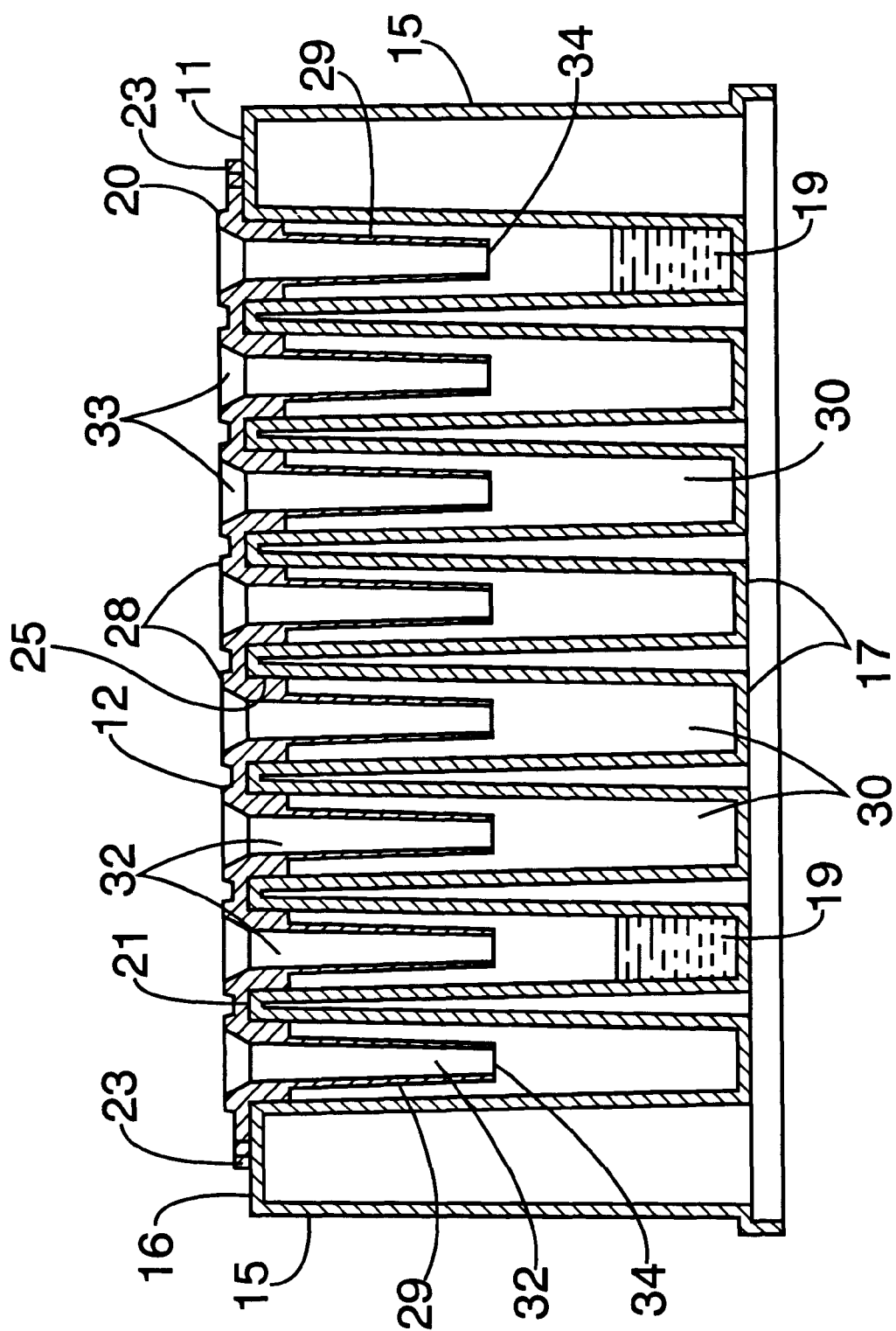
FIG. 7 is an elevation in cross section taken on the line 7—7 of FIG. 5 and looking in the direction of the arrows.
Figure 10:
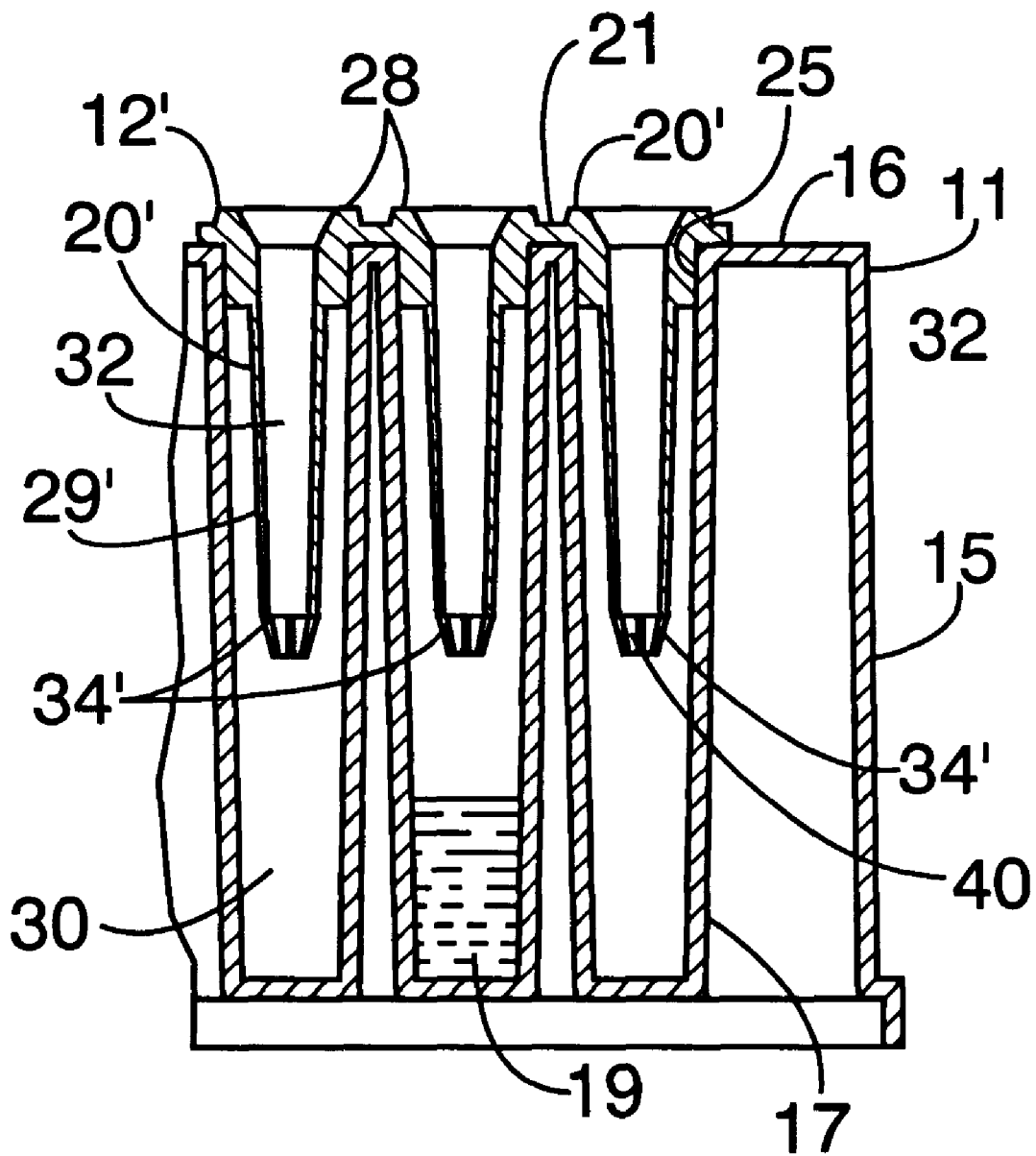
FIG. 10 is an elevation in cross section, similar to the view in FIG. 6, showing an alternate embodiment of the invention.
Figure 11:
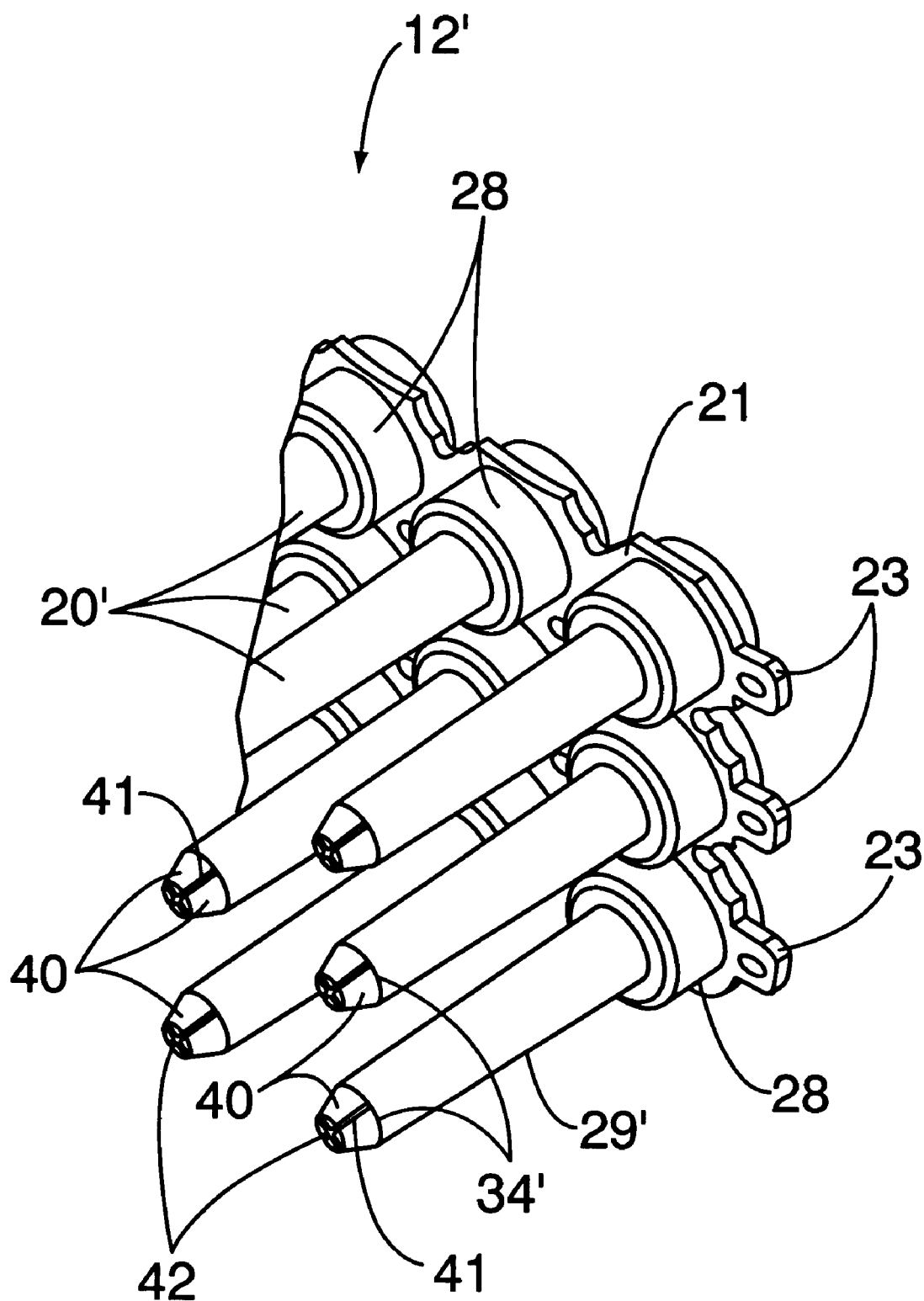
FIG. 11 is a pictorial view with parts broken away showing the FIG. 10 embodiment of the invention.
Figure 12:
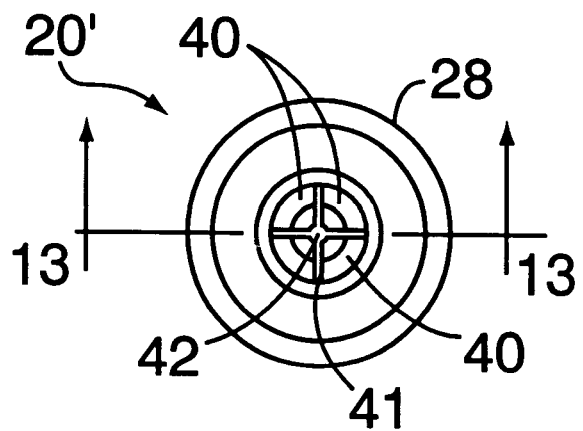
FIG. 12 is a bottom view of the well insert shown in FIG. 13.
Figure 13:
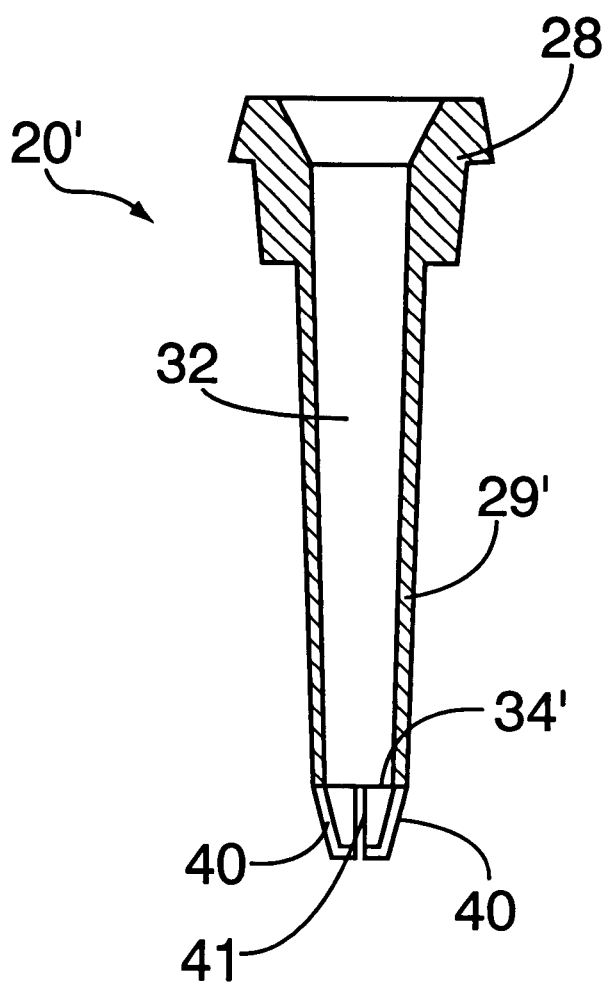
FIG. 13 is an elevation in cross section taken on the line 13—13 of FIG. 12 and looking in the direction of the arrows.
Figure 14:
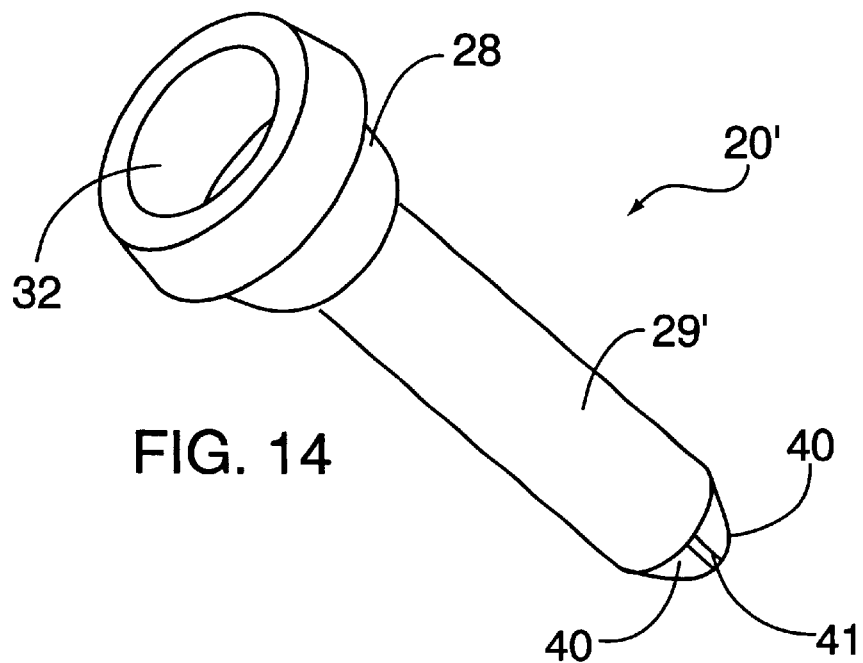
FIG. 14 is a pictorial view of the well insert shown in FIGS. 12 and 13.
Figure 15:
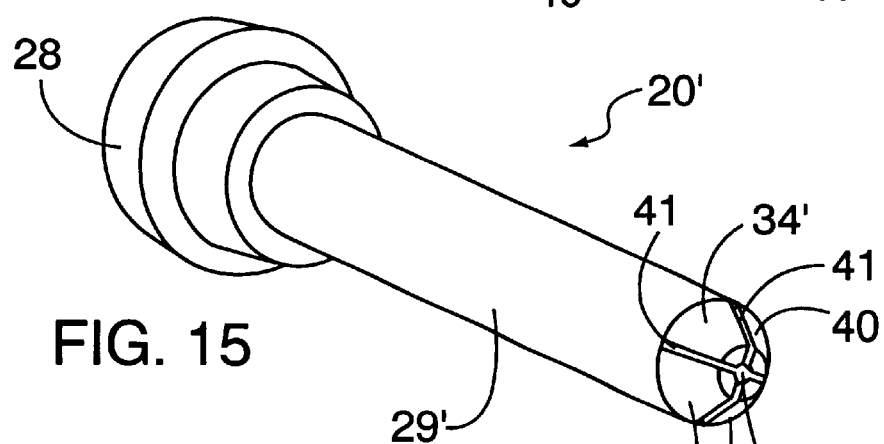
FIG. 15 is a pictorial view of the well insert shown in FIGS. 12–14.

Referring now to the drawings, microplate assembly 10 comprises microplate 11, four vent caps 12 and vent film 13. Microplate 11 includes a box-like frame having side walls 15 and rectangular top wall 16, which house an array of ninety-six wells 17 arranged in twelve rows and eight columns. Each vent cap 12 comprises a rectangular array of twenty-four well inserts 20 arranged in three rows and eight columns. Four sets of well inserts 20 mate with corresponding wells 17 in the manner illustrated in FIG. 2, such that each of the ninety-six wells 17 contains a corresponding well insert 20. Vent film 13 comprises an adhesive-backed, porous film that adheres to the upper surface of vent caps 12 in the manner depicted in FIG. 1.

Wells 17, which function as receptacles for liquid samples 19 (see FIGS. 8A–8C), are shaped like a conventional test tube, i.e., as a hollow, circular cylinder with open mouth 25. Mouths 25 lie in the plane of top wall 16 while the cylindrical axes of wells 17 extend parallel to each other and perpendicular to the plane of top wall 16. Microplate 11 illustrates a popular microplate configuration. However, as will become apparent from the following description, the present invention is applicable to a variety of conventional microplate configurations.

Vent caps 12 each comprise a plurality of well inserts 20 interconnected by perforated web 21. Each well insert 20 includes sealing plug 28 with attached vent tube 29. Passage 32 extends through vent tube 29 and sealing plug 28. Passage 32 terminates in vent 34 at its lower end. Vent tube 29, sealing plug 28 and the interior walls of well 17 form interior volume 30 in which liquid sample 19 is deposited. Liquid sample 19 will occupy and remain confined to a liquid-holding space within volume 30 for all orientations of well 17. Vent 34 communicates with interior volume 30 at a point outside of the liquid-holding space. FIGS. 8A–8C diagrammatically illustrate this feature. In FIG. 8A, which shows well 17 in an upright position, liquid sample 19 occupies a region of interior volume 30 that is spaced below vent 34. In FIG. 8B, which shows well 17 in an inverted position, liquid sample 19 occupies a region of interior volume 30 that is again spaced below vent 34. In FIG. 8C, which shows well 17 in an inclined position, liquid sample 19 continues to occupy a region of interior volume 30 that is again spaced below vent 34.

Passages 32, which pass through well inserts 20, include fluted aperture 33 at its upper end. Plug 28, vent tube 29 and passage 32 generally have circular cross-sections with a radial taper. Perforated web 21 attaches to plugs 28 to hold well inserts 20 in a rectangular array. A similar array of perforations 35 in web 21 appear amid well inserts 20. The underside of most plugs 28 includes notches 36, which provide sites where a rigid rod (not shown) may be inserted to help pry plugs 28 from their corresponding wells 17 when removing vent cap 12 from microplate 11.

Consequently, vent caps 12 function as multiple vented seals for interior volumes 30 of wells 17. Each well insert 20 couples with a different well 17 such that plug 28 forms a tight press-fit seal with the edge of mouth 25. With vent cap 12 properly coupled to wells 17, each plug 28 prevents liquid sample 19 from exiting the interior volume 30 via the seam at the interface between plug 28 and mouth 25. In addition, each vent 34 will permit the pressure within interior volume 30 to be equalized with the ambient pressure via passage 32, thereby avoiding forces that may dislodge plug 28.

Manufacturers may readily choose appropriate dimensions for vent caps 12 so that the location of liquid sample 19 will always be spaced from vent 34. Specifically, liquid sample 19 will remain in a liquid-holding space in interior volume 30 that will remain below vent 34 for all possible positions of microplate assembly 10. Consequently, sealing plug 28 and its associated vent tube 29 will function to prevent loss of liquid sample 19. Further, the shape and size of vent 34 and passage 32 make it difficult for liquid to exit passage 32 due to fluid surface tension. Therefore, during all but the most violent movements of microplate assembly 10, liquid sample 19 will remain in its liquid-holding space far removed from vent 34.

The effective volume of well 17 essentially equals the maximum volume that liquid sample 19 may occupy without engaging vent 34 for all possible orientations of microplate assembly 10. The effective volume may be maximized for a given well 17 by placing vent 34 at the centroid of interior volume 30. When vent 34 is placed at the centroid of interior volume 30, the maximum effective volume substantially equals one-half the interior volume 30.

As mentioned above, it is desirable that microplate assemblies 10 provide means for inhibiting evaporation of liquid samples 19. To this end, microplate assemblies 10 include adhesive vent films 13 which adhere to the upper surfaces of vent caps 12, as illustrated in FIG. 1. By blocking passage 32, vent films 13 inhibit evaporation by reducing air circulation within passages 32 and the interior volumes 30. Also, vent film 13, can block the entrance of contaminants into wells 17. Vent films 13 may be formed by coating a thin sheet of polyethylene with an appropriate adhesive. Vent films 13 may be rendered porous by punching relatively small holes in the adhesive sheets. The number of holes and their placement may be chosen so that each passage 32 will communicate with at least one hole. In addition, minimum sized vents 34 can also significantly inhibit evaporation.

Microplate assembly 10 includes features that make it suitable for use in a variety of processes. Passages 32 permit the addition of material to interior volume 30 without requiring that vent caps 12 be removed, altered or otherwise manipulated. Such materials may be added to wells 17 as a liquid, a gas or a solid. In the later case, of course, the solid must be dimensioned to permit movement through passage 32. As illustrated in FIG. 9, liquids may be injected into wells 17 with the aid of injection probe 24. Solids, e.g., pellets or powders, may also be deposited via passages 32. Gases may also be directed into wells 17 via passages 32 using probes or other gas injection apparatus to provide, for example, a special environment in volume 30.

Microplate assembly 10 is useful in either manual or automatic processes. For instance, passages 32 provide a convenient avenue through which material may be inserted manually into wells 17, with or without the use of probe 24 or other apparatus. In this regard, passages 32 may act as funnels to help lead the material into interior volume 30. On the other hand, most automation processes use one or more probes 24 to add material or remove material via suction. In this instance, fluted apertures 33 will aid the automation process by acting as self-centering guides that can easily direct probe 24 into passages 32. A splined probe or one that is narrower than vent 34 will allow venting to occur during liquid injection or aspiration. Alternatively, vents 34 may be fabricated with polygonal cross-sections to prevent round probes from inhibiting venting of interior volume 30.

As mentioned above, manufactures typically fabricate microplates from polystyrene, polycarbonate, polypropylene, Teflon, glass, ceramics or quartz. As such, vent caps 12 may be readily molded from a variety of compatible materials. In this regard, the materials of vent cap 12 must be such that plugs 28 will have sufficient resiliency to form a good press-fit seal with mouth 25. In addition, web 21 preferably flex to allow for easy positioning and removal of vent cap 12. Web 21 comprises end tabs 23, which may be gripped manually or mechanically when manipulating vent cap 12. As mentioned above, notches 36 provide additional assistance when removing vent cap 12 from wells 17.

While standard microplates come in a variety of sizes, most conventional microplates contain wells arranged in units of twenty-four, with each unit having a 3×8 well geometry. To render vent caps 12 useful with most conventional microplates, vent caps 12 preferably contain twenty-four well inserts 20 arranged in 3×8 geometry. As such, a user may apply one or more vent caps 12 to cover the wells in most conventional microplates. Moreover, a user may cut web 21 with an ordinary scissors to produce a well cap of a different shape and/or size. Likewise, a user may remove a single well insert 20 from vent cap 12 for use with an individual well 17.

Microplate assembly 10 will function suitably with most conventional mixing equipment. In many conventional processes, the well contents must be mixed. In most processes, the product is added first, the well is then sealed and, finally, the well contents are mixed. Some processes perform mixing with shakers that vibrate the microplate in a horizontal plane. Others turn or roll the microplate about a horizontal or inclined axis to effect mixing. In either case, when capping wells 17 with vent caps 12, a process can perform a mixing step immediately after adding a product without fear of loosing the product during mixing.

Consequently, a user can ship, synthesize, heat, shake and roll liquid samples 19 and not worry about loosing valuable product. Suppliers can feel comfortable about shipping their compounds in ready-to-use microplates. Freezing samples and dry shipping are avoided. Robotic equipment, for example, can manipulate microplate assemblies 10 into any desired position without spillage, thereby permitting a more efficient use of such equipment.

FIGS. 10–16 illustrate still a further modification designed to reduce evaporation, spillage, cross contamination and the like. FIGS. 10–16 show to 10 modified vent cap 12' comprising multiple well inserts 20' interconnected by perforated web 21. Each well insert 20' includes a vent tube 29' and an attached sealing plug 28 located at one end of vent tube 29'. Passages 32 extend axially through the centers of sealing plugs 28 and vent tubes 29'. Each vent tube 29' terminates at its free end with a partially covered vent 34'. Specifically, four resilient flaps 40 mount at the free end of each vent tube 29' to form vent 34'. Flaps 40 extend radially with respect to the axis of passage 32. Narrow slits 41 and a small axial opening 42 separate flaps 40 from each other. Manufacturers may readily fabricate flaps 40 by first molding each vent tube 29' with its free end closed. The closed end of each vent tube 29' may then be punctured, to form opening 42, and then cut with a sharp blade, to form slits 41.

Figure 16:
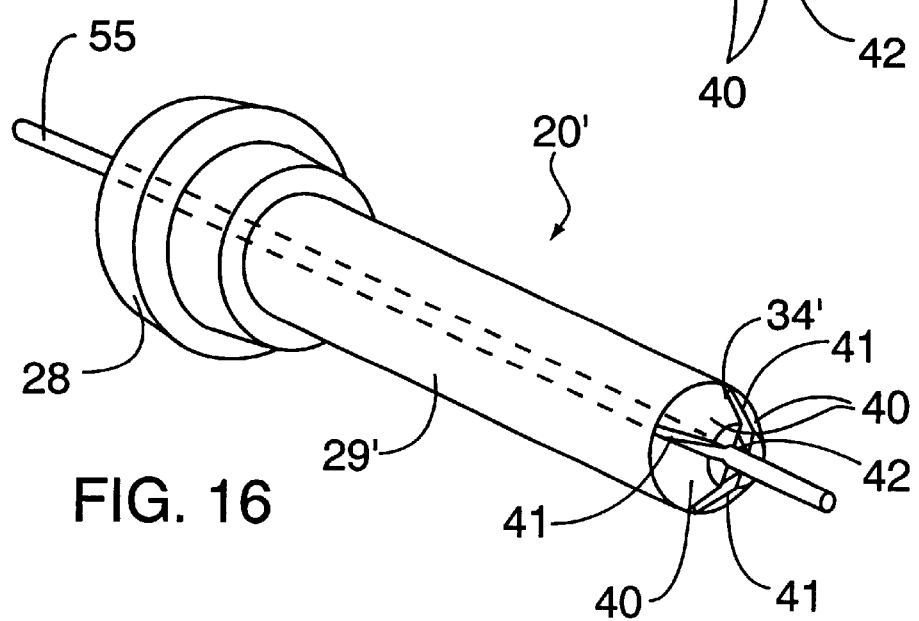
FIG. 16 is a pictorial view showing a probe inserted in the well insert shown in FIGS. 12–15.

While well inserts 20' effectively seal wells 17 to prevent the independent passage of liquid sample 19 from wells 17 for all possible positions of a microplate (see FIGS. 8A–8C), loss due to evaporation can be a real possibility. The nested flaps 40 will act as a barrier to help inhibit evaporation of liquid samples 19. In addition, during periods when a microplate is subjected to violent shaking, flaps 40 will help to prevent the loss of liquid sample 19 by blocking any liquid drops or spray from entering passage 32. As illustrated in FIG. 16, flaps 40 are sufficiently resilient to permit probe 55, such as an insertion needle, a pipette or a pellet plunger, to extend into the interior volumes 30. Upon withdrawal of probe 55, flaps 40 will return to their original nested position.

Of course, various other modifications and variations are contemplated and may obviously be resorted to in light of the present disclosure. It is to be understood, therefore, that within the scope of the appended claims, the invention may be practiced otherwise than as specifically described.

What is claimed is:

1. A method of sealing a vessel, to prevent independent passage of liquid from said vessel for all possible positions of the vessel, and venting said vessel, to equalize the gas pressure between interior and exterior of the vessel, and wherein said vessel has an opening and an interior volume with a liquid-holding space located therein, said method comprising:

mounting a cover over said opening to form a friction-tight impermeable seal between said cover and a surface of said opening;

forming a vent hole in said interior of said vessel outside said liquid-holding space for all possible positions of said vessel;

extending a tubular passage from said vent hole through said cover to the exterior of said vessel such that said vent hole communicates with said interior volume outside said liquid with interior volume outside said liquid-holding space and said exterior of said vessel; and placing a resilient barrier across said tubular passage to partially cover said vent hole wherein said resilient barrier defines an axial opening which forms a vent when not penetrated by a probe.

2. The method of claim 1 wherein the step of placing a resilient barrier includes resiliently mounting across said tubular passage a plurality of nested flaps which are spaced from each other by narrow slits to form said vent.

3. A method of sealing and venting multiple open wells contained in a multi-well microplate, each said well comprising a fluid vessel with an opening, an interior volume and a liquid-holding space located in said interior volume, said wells being sealed to prevent independent passage of liquid from said liquid-holding space to the exterior of said vessel, said method comprising the steps of:

inserting a plug having a flexible body with a resilient surface in each of said openings to form a friction-tight impermeable seal between said resilient surface and a surface of said opening;

forming a vent hole in the interior volume of each said well outside said liquid holding space for all possible positions of each said well;

extending a passage from each said vent hole through the flexible body of each said plug to the exterior of said wells;

placing a resilient barrier across each said tubular passage to partially cover each vent hole, wherein said resilient barrier defines an axial opening which forms a vent when not penetrated by a probe; and joining said plugs to each other with a flexible sheet in a planar array to match a pattern of said open wells.

4. The method of claim 3 wherein the step of placing a resilient barrier includes resiliently mounting across said tubular passage a plurality of nested flaps which are spaced from each other by narrow slits to form said vent.

5. The method of claim 4 wherein said forming step includes placing each said vent hole at substantially the centroid of said interior volume.

* * * * *